United States Patent
D'Agostino et al.

(10) Patent No.: US 11,850,323 B2
(45) Date of Patent: *Dec. 26, 2023

(54) IMPLANTABLE POLYMER FOR BONE AND VASCULAR LESIONS

(71) Applicant: 206 Ortho, Inc., Deerfield, NH (US)

(72) Inventors: Jeffrey A. D'Agostino, Deerfield, NH (US); Andrew J. Carter, Stow, MA (US); Craig M. Jones, Northborough, MA (US); Arthur C. Watterson, Nashua, NH (US)

(73) Assignee: 206 ORTHO, INC., Deerfield, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/113,430

(22) Filed: Dec. 7, 2020

(65) Prior Publication Data

US 2021/0178016 A1  Jun. 17, 2021

Related U.S. Application Data

(63) Continuation of application No. 15/156,782, filed on May 17, 2016, now Pat. No. 10,857,261, which is a continuation of application No. 14/193,619, filed on Feb. 28, 2014, now abandoned, which is a continuation of application No. 13/452,273, filed on Apr. 20, 2012, now abandoned, which is a continuation-in-part of application No. PCT/US2011/057124, filed on Oct. 20, 2011.

(60) Provisional application No. 61/394,968, filed on Oct. 20, 2010.

(51) Int. Cl.
| | |
|---|---|
| *A61L 27/18* | (2006.01) |
| *A61K 9/00* | (2006.01) |
| *A61K 47/34* | (2017.01) |
| *A61L 27/26* | (2006.01) |
| *A61L 27/44* | (2006.01) |
| *A61L 27/46* | (2006.01) |
| *A61L 27/48* | (2006.01) |
| *A61L 27/56* | (2006.01) |
| *A61L 27/16* | (2006.01) |
| *A61L 27/54* | (2006.01) |
| *A61L 27/58* | (2006.01) |
| *A61L 27/52* | (2006.01) |

(52) U.S. Cl.
CPC ............ *A61L 27/18* (2013.01); *A61K 9/0024* (2013.01); *A61K 47/34* (2013.01); *A61L 27/16* (2013.01); *A61L 27/26* (2013.01); *A61L 27/446* (2013.01); *A61L 27/46* (2013.01); *A61L 27/48* (2013.01); *A61L 27/52* (2013.01); *A61L 27/54* (2013.01); *A61L 27/56* (2013.01); *A61L 27/58* (2013.01); *A61L 2300/406* (2013.01); *A61L 2300/604* (2013.01); *A61L 2400/06* (2013.01); *A61L 2430/02* (2013.01)

(58) Field of Classification Search
CPC ....... A61K 9/0024; A61K 47/34; A61L 27/18; A61L 27/16; A61L 27/26; A61L 27/446; A61L 27/46; A61L 27/48; A61L 27/52; A61L 27/54; A61L 27/56; A61L 27/58; A61L 2300/406; A61L 2300/604; A61L 2400/06; A61L 2430/02
See application file for complete search history.

(56) References Cited

U.S. PATENT DOCUMENTS

| | | |
|---|---|---|
| 534,293 A | 2/1895 | Stevens |
| 2,902,462 A | 9/1959 | Harry et al. |
| 2,951,823 A | 9/1960 | Hubert |
| 2,961,374 A | 11/1960 | Hans et al. |
| 3,830,750 A | 8/1974 | Wellman |
| 4,241,537 A | 12/1980 | Wood |
| 4,356,228 A | 10/1982 | Kobayashi et al. |
| 4,645,503 A | 2/1987 | Lin et al. |
| 4,653,487 A | 3/1987 | Maale |
| 4,843,112 A | 6/1989 | Gerhart et al. |
| 4,916,193 A | 4/1990 | Tang et al. |
| 4,919,679 A | 4/1990 | Averill et al. |
| 4,955,911 A | 9/1990 | Frey et al. |
| 4,993,410 A | 2/1991 | Kimsey |

(Continued)

FOREIGN PATENT DOCUMENTS

| | | |
|---|---|---|
| EP | 0656215 | 6/1995 |
| EP | 0677297 | 10/1995 |

(Continued)

OTHER PUBLICATIONS

Baravarian et al., Advancements in Bone Fixation Utilizing Novel Biointegrative Fixation Technology, Clin Podiatr Med Surg, 2018, vol. 35, pp. 53-62.
https://bonnieplants.com/growing/growing-cauliflower, 2013.
https://en.wikipediaorg/wiki/Fracture_toughness, Dec. 15, 2005.
http://v1Avw.iflscience.com/health-and-medicine/new-drug-delivery-system-co uld-replace-injections, Oct. 4, 2014.

(Continued)

*Primary Examiner* — Blessing M Fubara
(74) *Attorney, Agent, or Firm* — Grossman, Tucker, Perreault & Pfleger, PLLC

(57) ABSTRACT

A solidifying prepolymeric implant composition comprising a biocompatible prepolymer and an optional filler. One such implant composition is a polyurethane implant composition comprising an isocyanate, such as hydroxymethylenediisocyanate (HMDI) and an alcohol, such as polycaprolactone-diol (PCL diol). The compositions of the invention are useful for improving bone structure in patients by applying the solidifying implant composition to bone, reinforcing bone structure, improving load bearing capacity and/or aiding healing of microfractures.

20 Claims, No Drawings

(56) References Cited

U.S. PATENT DOCUMENTS

| | | | |
|---|---|---|---|
| 5,010,145 | A | 4/1991 | Ikada et al. |
| 5,026,373 | A | 6/1991 | Ray et al. |
| 5,047,054 | A | 9/1991 | Vijayan et al. |
| 5,064,427 | A | 11/1991 | Burkinshaw |
| 5,126,170 | A | 6/1992 | Zwiener et al. |
| 5,175,199 | A | 12/1992 | Asano et al. |
| 5,190,549 | A | 3/1993 | Miller et al. |
| 5,190,550 | A | 3/1993 | Miller et al. |
| 5,236,741 | A | 8/1993 | Zwiener et al. |
| 5,243,012 | A | 9/1993 | Wicks et al. |
| 5,336,699 | A | 8/1994 | Cooke et al. |
| 5,352,230 | A | 10/1994 | Hood |
| 5,362,834 | A | 11/1994 | Schapel et al. |
| 5,401,693 | A | 3/1995 | Bauer et al. |
| 5,409,492 | A | 4/1995 | Jones et al. |
| 5,443,471 | A | 8/1995 | Swajger |
| 5,458,641 | A | 10/1995 | Ramirez Jimenez |
| 5,476,466 | A | 12/1995 | Barrette et al. |
| 5,489,704 | A | 2/1996 | Squiller et al. |
| 5,501,706 | A | 3/1996 | Arenberg |
| 5,514,136 | A | 5/1996 | Richelsoph |
| 5,514,137 | A | 5/1996 | Coutts |
| 5,516,873 | A | 5/1996 | Hicks et al. |
| 5,549,679 | A | 8/1996 | Kuslich |
| 5,580,945 | A | 12/1996 | Wade et al. |
| 5,591,453 | A | 1/1997 | Ducheyne et al. |
| 5,597,930 | A | 1/1997 | Wicks et al. |
| 5,623,045 | A | 4/1997 | Zwiener et al. |
| 5,633,389 | A | 5/1997 | Jonsson et al. |
| 5,644,049 | A | 7/1997 | Giusti et al. |
| 5,681,872 | A | 10/1997 | Erbe |
| 5,683,395 | A | 11/1997 | Miktiail |
| 5,725,580 | A | 3/1998 | Cloutier et al. |
| 5,739,176 | A | 4/1998 | Dunn et al. |
| 5,785,642 | A | 7/1998 | Wallace et al. |
| 5,821,326 | A | 10/1998 | Kurek et al. |
| 5,827,289 | A | 10/1998 | Reiley et al. |
| 5,847,195 | A | 12/1998 | Roesler |
| 5,849,015 | A | 12/1998 | Haywood et al. |
| 5,852,203 | A | 12/1998 | Jonsson et al. |
| 5,863,551 | A | 1/1999 | Woerly |
| 5,899,907 | A | 5/1999 | Jolinson |
| 5,916,585 | A | 6/1999 | Cook et al. |
| 5,951,564 | A | 9/1999 | Schroder et al. |
| 5,989,259 | A | 11/1999 | Penenberg et al. |
| 6,027,742 | A | 2/2000 | Lee et al. |
| 6,086,556 | A | 7/2000 | Hamilton et al. |
| 6,107,436 | A | 8/2000 | Goeb et al. |
| 6,110,179 | A | 8/2000 | Flivik et al. |
| 6,113,605 | A | 9/2000 | Storer |
| 6,127,597 | A | 10/2000 | Beyar et al. |
| 6,139,963 | A | 10/2000 | Fujii et al. |
| 6,165,177 | A | 12/2000 | Wilson et al. |
| 6,168,777 | B1 | 1/2001 | Greff et al. |
| 6,183,870 | B1 | 2/2001 | Hergenrother et al. |
| 6,228,092 | B1 | 5/2001 | Mikhail |
| 6,238,435 | B1 | 5/2001 | Meulink et al. |
| 6,270,502 | B1 | 8/2001 | Stulberg |
| 6,274,164 | B1 | 8/2001 | Novich |
| 6,306,243 | B1 | 10/2001 | Clark et al. |
| 6,355,829 | B2 | 3/2002 | Roesler et al. |
| 6,447,514 | B1 | 9/2002 | Stalcup et al. |
| 6,511,748 | B1 | 1/2003 | Barrows |
| 6,521,736 | B2 | 2/2003 | Watterson et al. |
| 6,524,327 | B1 | 2/2003 | Spacek |
| 6,530,958 | B1 | 3/2003 | Cima et al. |
| 6,548,002 | B2 | 4/2003 | Gresser et al. |
| 6,602,293 | B1 | 8/2003 | Biermann et al. |
| 6,626,913 | B1 | 9/2003 | McKinnon et al. |
| 6,679,890 | B2 | 1/2004 | Margulies et al. |
| 6,884,264 | B2 | 4/2005 | Spiegelberg et al. |
| 6,962,963 | B2 | 11/2005 | Kumar et al. |
| 7,037,311 | B2 | 5/2006 | Parkinson et al. |
| 7,255,712 | B1 | 8/2007 | Steinberg |
| 7,368,503 | B2 | 5/2008 | Hale |
| 7,494,491 | B2 | 2/2009 | Fankhauser et al. |
| 7,517,539 | B1 | 4/2009 | Lee et al. |
| 7,682,335 | B2 | 3/2010 | Pepper et al. |
| 7,708,979 | B2 | 5/2010 | Lowman et al. |
| 7,754,782 | B2 | 7/2010 | Heckroth et al. |
| 7,781,038 | B2 | 8/2010 | Hamilton et al. |
| 7,806,900 | B2 | 10/2010 | Rabiner |
| 7,879,107 | B2 | 2/2011 | Knothe Tate et al. |
| 7,964,206 | B2 | 6/2011 | Suokas et al. |
| 8,007,498 | B2 | 8/2011 | Mische |
| 8,128,626 | B2 | 3/2012 | Justin |
| 8,137,777 | B2 | 3/2012 | Chen |
| 8,147,492 | B2 | 4/2012 | Justin et al. |
| 8,162,943 | B2 | 4/2012 | Justin et al. |
| 8,167,881 | B2 | 5/2012 | Justin |
| 8,246,371 | B2 | 8/2012 | Emerson |
| 8,246,628 | B2 | 8/2012 | Rabiner |
| 8,348,956 | B2 | 1/2013 | Rabiner |
| 8,366,711 | B2 | 2/2013 | Rabiner et al. |
| 8,492,484 | B2 | 7/2013 | Lorenz |
| 8,497,342 | B2 | 7/2013 | Chen et al. |
| 8,512,338 | B2 | 8/2013 | Rabiner et al. |
| 8,524,856 | B2 | 9/2013 | Krishnaswamy et al. |
| 8,546,456 | B2 | 10/2013 | Rose et al. |
| 8,722,783 | B2 | 5/2014 | Rose et al. |
| 8,834,468 | B2 | 9/2014 | Justin |
| 8,870,965 | B2 | 10/2014 | Rabiner et al. |
| 8,912,149 | B1 | 12/2014 | Rawat et al. |
| 9,320,601 | B2 | 4/2016 | D'Agostino et al. |
| 9,381,277 | B2 | 7/2016 | Lehtonen et al. |
| 9,492,210 | B2 | 11/2016 | Rains et al. |
| 10,010,609 | B2 | 7/2018 | D'Agostino et al. |
| 10,028,776 | B2 | 7/2018 | D'Agostino et al. |
| 10,857,261 | B2 * | 12/2020 | D'Agostino ............ A61L 27/58 |
| 2002/0150604 | A1 | 10/2002 | Yi et al. |
| 2003/0044467 | A1 | 3/2003 | Brodbeck et al. |
| 2003/0114552 | A1 | 6/2003 | Schacht |
| 2004/0010261 | A1 | 1/2004 | Hoag et al. |
| 2004/0010262 | A1 | 1/2004 | Parkinson et al. |
| 2004/0028655 | A1 | 2/2004 | Nelson et al. |
| 2004/0078090 | A1 | 4/2004 | Binette et al. |
| 2004/0082954 | A1 | 4/2004 | Teitelbaum et al. |
| 2004/0220672 | A1 | 11/2004 | Shadduck |
| 2004/0221615 | A1 | 11/2004 | Postupack et al. |
| 2004/0230309 | A1 | 11/2004 | Dimauro et al. |
| 2004/0242722 | A1 | 12/2004 | Rose et al. |
| 2004/0265355 | A1 | 12/2004 | Shalaby |
| 2005/0010231 | A1 | 1/2005 | Myers |
| 2005/0055094 | A1 | 3/2005 | Kuslich |
| 2005/0081750 | A1 | 4/2005 | Xu et al. |
| 2005/0136764 | A1 | 6/2005 | Sherman et al. |
| 2005/0142163 | A1 | 6/2005 | Hunter |
| 2005/0208094 | A1 | 9/2005 | Armitage et al. |
| 2005/0233062 | A1 | 10/2005 | Hossainy et al. |
| 2006/0064164 | A1 | 3/2006 | Thelen et al. |
| 2006/0095138 | A1 | 5/2006 | Truckai et al. |
| 2006/0100174 | A1 | 5/2006 | Hu et al. |
| 2006/0141101 | A1 | 6/2006 | Chen et al. |
| 2006/0184250 | A1 | 8/2006 | Bandoh et al. |
| 2006/0200150 | A1 | 9/2006 | Ilomaki et al. |
| 2006/0208393 | A1 | 9/2006 | Karmaker et al. |
| 2007/0059281 | A1 | 3/2007 | Moseley et al. |
| 2007/0191963 | A1 | 8/2007 | Winterbottom |
| 2007/0208134 | A1 | 9/2007 | Hunter |
| 2007/0255422 | A1 | 11/2007 | Wei et al. |
| 2008/0004628 | A1 | 1/2008 | White |
| 2008/0051797 | A1 | 2/2008 | Surrna et al. |
| 2008/0160259 | A1 | 7/2008 | Nielson et al. |
| 2008/0172061 | A1 | 7/2008 | Ragbir |
| 2008/0206716 | A1 | 8/2008 | Asgary |
| 2008/0221576 | A1 | 9/2008 | Keller |
| 2008/0228284 | A1 | 9/2008 | Fritz et al. |
| 2008/0255560 | A1 | 10/2008 | Myers et al. |
| 2009/0099267 | A1 | 4/2009 | Kumar et al. |
| 2009/0148487 | A1 * | 6/2009 | Siedler ............ A61L 27/58 |
| | | | 424/499 |
| 2009/0182425 | A1 | 7/2009 | Duda et al. |
| 2009/0204196 | A1 | 8/2009 | Weber |
| 2010/0076503 | A1 | 3/2010 | Beyar et al. |

(56) References Cited

U.S. PATENT DOCUMENTS

| | | |
|---|---|---|
| 2010/0099779 A1 | 4/2010 | Hnojewyj et al. |
| 2010/0137491 A1 | 6/2010 | Rose et al. |
| 2010/0168798 A1 | 7/2010 | Clineff et al. |
| 2010/0248260 A1 | 9/2010 | Ban et al. |
| 2010/0318085 A1 | 12/2010 | Austin et al. |
| 2010/0330260 A1 | 12/2010 | McKay |
| 2010/0331850 A1 | 12/2010 | Rabiner |
| 2011/0013958 A1 | 1/2011 | Shona et al. |
| 2011/0066252 A1 | 3/2011 | Hanssen et al. |
| 2011/0159071 A1 | 6/2011 | Cool et al. |
| 2011/0184115 A1 | 7/2011 | Debras et al. |
| 2011/0184530 A1 | 7/2011 | Datta et al. |
| 2011/0189414 A1 | 8/2011 | Whitehouse |
| 2011/0237704 A1 | 9/2011 | Guelcher et al. |
| 2011/0244017 A1 | 10/2011 | Kleiner et al. |
| 2012/0028047 A1 | 2/2012 | Imai et al. |
| 2012/0029102 A1 | 2/2012 | Rose et al. |
| 2012/0040002 A1 | 2/2012 | Letitonen et al. |
| 2012/0048769 A1 | 3/2012 | Sivik et al. |
| 2012/0059376 A1 | 3/2012 | Rains et al. |
| 2012/0095463 A1 | 4/2012 | Rains et al. |
| 2012/0101593 A1 | 4/2012 | D'Agostino et al. |
| 2012/0149844 A1 | 6/2012 | Whitehouse |
| 2012/0203264 A1 | 8/2012 | Karwa et al. |
| 2012/0238523 A1 | 9/2012 | Cool et al. |
| 2012/0263797 A1 | 10/2012 | D'Agostino et al. |
| 2012/0310368 A1 | 12/2012 | Voisard et al. |
| 2012/0315225 A1 | 12/2012 | Porbeni et al. |
| 2013/0045249 A1 | 2/2013 | Cool et al. |
| 2013/0065046 A1 | 3/2013 | Krishnaswamy |
| 2013/0071443 A1 | 3/2013 | Cool et al. |
| 2013/0171397 A1 | 7/2013 | Ghost et al. |
| 2013/0219965 A1 | 8/2013 | Allan et al. |
| 2013/0233545 A1 | 9/2013 | Mahoney et al. |
| 2013/0253661 A1 | 9/2013 | D'Agostino et al. |
| 2013/0323468 A1 | 12/2013 | Myers et al. |
| 2014/0030536 A1 | 1/2014 | Krishnaswamy |
| 2014/0046454 A1 | 2/2014 | Rose et al. |
| 2014/0079789 A1 | 3/2014 | Pomrink et al. |
| 2014/0127500 A1 | 5/2014 | Carberry et al. |
| 2014/0178328 A1 | 6/2014 | D'Agostino et al. |
| 2014/0235754 A1 | 8/2014 | Rose et al. |
| 2015/0328251 A1 | 11/2015 | Cool et al. |
| 2016/0346435 A1 | 12/2016 | D'Agostino et al. |

FOREIGN PATENT DOCUMENTS

| | | |
|---|---|---|
| EP | 0927214 | 7/2007 |
| EP | 2223707 | 9/2010 |
| WO | 89/00431 | 1/1989 |
| WO | 92/20738 | 11/1992 |
| WO | 98/19617 | 5/1998 |
| WO | 01/64139 | 9/2001 |
| WO | 2004/073563 | 9/2004 |
| WO | 2004/103208 | 12/2004 |
| WO | 2005/112804 | 12/2005 |
| WO | 2007/082186 | 7/2007 |
| WO | 2008/067531 | 6/2008 |
| WO | 2008/096363 | 8/2008 |
| WO | 2010/011943 | 1/2010 |
| WO | 2010/122098 | 10/2010 |
| WO | 2011/071453 | 6/2011 |
| WO | 2013/012731 | 1/2013 |
| WO | 2013/130877 | 9/2013 |
| WO | 2013/184822 | 12/2013 |
| WO | 2013/184836 | 12/2013 |
| WO | 2014/028943 | 2/2014 |
| WO | 2014/190289 | 11/2014 |
| WO | 2015/172101 | 11/2015 |
| WO | 2015/175682 | 11/2015 |
| WO | 2016/035088 | 3/2016 |
| WO | 2016/035089 | 3/2016 |
| WO | 2016/103049 | 6/2016 |
| WO | 2017/155956 | 9/2017 |
| WO | 2018/002917 | 1/2018 |

OTHER PUBLICATIONS

M. Barry et al., Flexible Intramedullary Nails for Fractures in Children, Journal of Bone & Joint Surgery, 2004, pp. 947-950.

T. Hirvikorpi et al., Enhanced Water Vapor Barrier Properties for Biopolymer Films by Polyelectrolyte Multilayer and Atomic Layer Deposited Al2O3 Double-Coating. Applied Surface Science, 2011, vol. 257, No. 22, pp. 9451-9454.

J.-W. Rhim et al., Bio-Nanocomposites for Food Packaging Applications, Progress in Polymer Science, 2013, vol. 38, pp. 1629-1652.

M. L. Williams et al., The Temperature Dependence of Relaxation Mechanisms in Amorphous Polymers and Other Glass-Forming Liquids, Journal of the American Chemical Society, 1955, vol. 77, pp. 370·,-3707.

R Shogren, Water Vapor Permeability of Biodegradable Polymers, Journal of Environmental Polymer Degradation, 1997, vol. 5, No. 2, pp. 91-95.

Bibekananda, D. et al., Biodegradable Hyperbranced Epoxy From Castor Oil-Based Hyperbranched Polyester Polyoi, ACS Sustainabie Chemistry & Engineering, Mar. 2014, vol. 2, No. 3, pp. 445-453.

http://wernerblank.com/equat/ViSCTEMP3.htm, Oct. 2010.

http://wernerblank.com/polyur/chemistry/isocyanate/isocyanat_overview.htm, Nov. 2006.

Feng, X. et al., Overview of Advances in Sugar-Based Polymers, Polymers for Advanced Technologies, Nov. 10, 2010, vol. 22, pp. 139-150.

Chen et al., Comparison of biodegradable and metallic tension-band fixation for patella fractures: 38 patients followed for 2 years, Acta Orthopaedica Scandinavica, 1998.

Dow Answer Center, Dow Polyurethanes—Prepolymer Definition, Oracle, 2014.

Middleton et al., Synthetic biodegradable polymers as orthopedic devices, Biomaterials, 2000.

\* cited by examiner

IMPLANTABLE POLYMER FOR BONE AND VASCULAR LESIONS

REFERENCE TO RELATED APPLICATIONS

This application is a continuation-in-part of International Application PCT/US2011/057124 filed Oct. 20, 2011 entitled "IMPLANTABLE POLYMER FOR BONE AND VASCULAR LESIONS" which claims the priority of U.S. Provisional Patent Application No. 61/394,968 filed Oct. 20, 2010 also entitled "IMPLANTABLE POLYMER FOR BONE AND VASCULAR LESIONS", each of which is incorporated herein in their entirety by reference.

BACKGROUND OF THE INVENTION

1. Technical Field

The present invention relates to compositions and methods of treating bone fractures. In particular, the present invention relates to compositions made of polymers and ceramics for treating bone fractures, lesions, voids, and temporary or permanent fixation of implants. Additionally, the present invention relates to compositions made of polymers for treating vascular lesions and visceral fistulas.

2. Background Art

Progressive loss of bone density and thinning of bone tissue are characteristics of osteoporosis, the most common type of bone disease affecting 10 million Americans. Although regular exercise with daily intake of vitamin and mineral supplements can help alleviate the symptoms of osteoporosis, they do not provide wholesome treatment to those experiencing osteoporosis-induced fractures. The early stages of this disease yield little to no symptoms; however, as the disease progresses to late stage, patients begin to experience various symptoms, including: low back pain, bone pain, fractures with little to no trauma, and kyphosis. Bone mineral testing quantitatively measures bone density within a patient. These tests can accurately predict the risk for bone fractures in the future. From these tests, high-risk patients can be prescribed a variety of different medications, including, but not limited to: bisphosphonates, calcitonin, hormone replacement therapy, parathyroid hormone, raloxifene, or advised regular exercise with a balanced, nutritional diet.

Although these medications and routine changes can help prevent fractures, it cannot reverse pre-collapsed vertebrae, or regenerate large quantity bone defects created by trauma, infection, skeletal abnormalities or tumor resection. The aforementioned problems go beyond normal potential for self-healing within the bones; therefore, clinical treatment becomes necessary.

Clinical treatment for collapsed vertebrae includes vertebroplasty or kyphoplasty. Within vertebroplasty, physicians inject a cement mixture into the fractured segment of the vertebrae, whereas in kyphoplasty, a balloon is inserted before cement injection to create a cavity or space. Once the balloon is removed, the cement can be injected into the cavity. Although these clinical procedures allow the patient to regain functional abilities without pain, they carry various risks with them as well, including: risk of infection, risk of orthopedic cement leakage out of vertebral body that can cause pulmonary edema if cement migrated to the lungs, secondary fracture of the adjacent vertebra if cement leaks into the disk space, and neurological symptoms if cement leaks onto spinal nerves.

Clinical treatment for overuse-induced, trauma-induced, infection-induced, osteoporosis-induced or tumor-induced fractures includes rest, reducing the load subjected to the fracture, insertion of one or more screws across the fracture point, insertion of a steel plate held by screws across the fracture point, insertion of a long metal rod driven down the shaft of the bone, or, in severe cases, bone grafting and joint replacement will be considered. The most common problem that arises from osteoporosis-induced fractures is failure of fixation of the aforementioned screws, metal plate, or rod due to the decreased bone density in the osteoporotic patient.

Clinical treatment for bone injuries in otherwise healthy bones, such as the young and active patient with, for example, a stress fracture will be considered. This population can be particularly difficult to treat since, after treatment, the patient is more likely to put significant tension on the bone due to a higher level of activity than with an older and/or more sedentary patient. This is particularly important for long bones where both compressive and tensile stress is put on the bone. See U.S. Provisional Patent Application No. 61/604,632 filed Feb. 29, 2012 entitled "SPLINT INJECTION", which is incorporated by reference in its entirety.

Surgeons attempt to decrease failure of fixation by reinforcement of the surgical prosthesis with bone cement. This cement fills in the void between the prosthesis and the bone.

Currently, bone cements are supplied as two-component materials. One component consists of a powder; the second component consists of a liquid. The powder component is made from, but not limited to, poly(methyl-methacrylate) (PMMA), PMMA with various salt additives, calcium phosphate, and bioactive glass substitutes. The liquid component is made from, but not limited to, a stabilizer, an inhibitor, and a MMA monomer. These two components are mixed together in a certain ratio under vacuum-sealed conditions. Once the mixture is homogeneous, the bone cement is injected into a void and allowed to harden.

The optimal bone cement has properties that mimic natural human bone that include, but are not limited to, cement pore size between 50 microns to 150 microns, high pore connectivity, osteoconductive properties, and comparable Young's modulus (stiffness/hardness) to that of natural bone.

The disadvantage of current PMMA based bone cements are their physical properties, lack of osteoconductivity, and resorption. This prevents the PMMA from being properly integrated into the bone, and instead, the PMMA is encapsulated by a connective tissue layer. Furthermore, PMMA based bone cements attain relatively high temperatures that can exceed 80 degrees C. while setting. Surrounding tissues exposed to such high heat undergo thermal tissue necrosis. Additionally, PMMA based bone cements are known to have a Young's modulus greater that of natural bone, therefore, natural stresses experienced by the bone during motion induced by the patient are loaded into the cement, rather than the bone. When the natural bone stops receiving mechanical signals from daily movement by the patient, stress shielding occurs, where bone remodeling comes to a standstill and worsens osteoporotic weakening of the bone. This can lead to a revision surgery. The difficulty and length of the revision surgery is increase by the difficulty in removing current bone cements.

The disadvantage of PMMA infused with various salt additives has similar disadvantages as aforementioned for sole PMMA based bone cements.

Calcium phosphate and other ceramic cement based bone substitutes have been somewhat successful over PMMA based cements in avoiding thermal tissue necrosis and creating a more osteoconductive, regenerative scaffold for bone growth. The main disadvantage of calcium phosphate and other ceramic cement based bone substitutes is their low tensile strength. This limits their ability to be used in any location where there is a tensile component of the loading on the bone, such as on long bones such as the tibia. Their thicker viscosity is an additional limitation. This limits their ability to be pushed though small lumen used in minimally invasive treatment and percutaneous injections.

Bioactive glass bone substitutes have also been investigated as an alternative. The disadvantage of bioactive glass substitutes includes, but is not limited to, poor resorption in natural bone. Although bioactive glass substitutes possess superior mechanical strength, varying pore sizes between 50-150 microns, and high connectivity between pores, the substitute has a poor resorption rate, and therefore, the natural bone has hindered growth. Similar to the ceramic cements the glasses have very poor tensile properties.

There are several challenges with current liquid embolic technologies. Frequently embolization of vascular lesions is required to treat, reduce blood flow prior to or following incomplete surgical treatment of various vascular diseases. Currently, there are not effective treatments available or available treatment options are dangerous, painful, and debilitating. The available methods for endovascular treatment of vascular lesions are often ineffective and require numerous re-treatments. The buildup of radioopaque material from multiple injections, large injections, or subsequent embolization procedures makes imaging and safely navigating the vascular lesion more difficult, takes longer, and limits the imaging options. Difficulty visualizing the vascular lesion leads to increased procedural times, radiation dose to the patient and surgical staff, and treatment cost. Patients frequently get radiation burns and lose hair from the prolonged exposure.

Current devices approved for treatment and/or occlusion of venous varices, vascular tumors, and traumatic vessel injury are awkward to handle, lack control, and are often incomplete or require multiple treatments. Endovascular treatment of brain arteriovenous malformations often does not completely and durably occlude the lesion. More invasive and dangerous treatment with open neurovascular surgery or single, high dose stereotactic radiation (which may be incompletely effective, or require a significant therapeutic interval during which the patient is not protected from cerebral hemorrhage) can be required for these patients who cannot be completely and durably treated by minimally invasive methodologies. Endovascular devices and surgical repair of aneurysms may not completely and durably occlude certain lesions and may require retreatment.

The radiopaque materials used in embolic agents can spark and ignited the embolic material in the patient during surgical resection. Surgeons frequently use mono cautery during open surgical procedures. The mono cautery initially causes the radiopaque particles to spark followed by the embolic material catching on fire. The fire can last for several seconds after the surgeon stops using the cauterization.

The solvent volume used in current liquid embolic agents is not safe or compatible for many procedures. The product, Onyx®, which is an ethylene vinyl alcohol copolymer dissolved in DMSO, uses DMSO at concentration from 94% to 80% by molecular weight. DMSO affects nerves by inhibiting cholinesterase. The effect of DMSO on nerves is typically seen after a vessel is occluded; when the DMSO concentration builds up in the surrounding tissue. DMSO can also cause an acute tissue response. This was demonstrated when Onyx did not meet the FDA requirement of a USP 7-day muscle implant evaluation because implantation resulted in an acute tissue response. DMSO can cause spontaneous skeletal muscle fasciculations. Making visualization difficult for the surgeon and causing pain for the patient. These procedures are converted to an intubated procedure increasing the risk and cost of the treatment. DMSO ability to lower the vagal threshold could be a cause of the bradycardia seen when using Onyx near the valgus nerve.

Open surgical treatment is dangerous, debilitating and more costly. Currently, no optimal and safe device exists for endovascular treatment for many arteriovenous malformations, arteriovenous fistulae, or visceral and/or viscerocutaneous fistulae.

Therefore, there remains a need for a method for developing a bone cement, scaffold, which caters to the aforementioned problems with current bone cement technologies and aims to incorporate: a broad range of drug-eluting properties including using nano-particle for delivery, infusion of radio-opaque components, biodegradability of the bone cement, improved load bearing functionality particularly to tensile loads, and elimination of the two-component dry and wet based system for mixing bone cements. Furthermore, there remains a need for a treatment for vascular diseases that is less invasive, allows for more precise control, improved visibility, and more efficacious treatment.

SUMMARY OF THE INVENTION

The present invention provides a solidifying implant composition for treating fractures, lesions, voids, and temporary or permanent fixation of implants. In one aspect the invention concerns biodegradable polymeric compositions for bone augmentation or treatment of bone fractures, such as incomplete fractures and fatigue stress fractures. The compositions can include polymeric solutions, which harden upon solvent precipitation or evaporation or can be polymer compositions without solvents, e.g. monomeric or polymeric precursors that can polymerize in situ, with or without help from crosslinkers or solvents.

In some embodiments, the solidifying prepolymeric implant composition can be a biocompatible prepolymer combined with an optional filler. The hydrophobicity of this composition can be controlled. The viscosity of the prepolymeric implant composition, prior to solidification must be sufficiently low for injection through a 14-gauge needle. In some embodiments, it must be injectable through a 16-gauge needle, an 18-gauge needle, a 20-gauge needle, or a 22-gauge needle.

In some embodiments, the composition comprises a filler. In some embodiments, the composition comprises SN ethylhexanoate (SN-Oct). In some embodiments, the composition comprises beta-tricalcium phosphate ($\beta$-TCP). In some embodiments, the composition comprises calcium carbonate. In some embodiments, the composition comprises a liquid contrast agent chosen from the group consisting of Ethiodol, Tantalum, Barium Sulfate, and Nickel-Titanium.

In some embodiments, the solidifying implant composition, when solidified possesses a compressive stiffness of between about 0.25 and about 20 GPa, or more preferably between about 0.30 and about 2 GPa, or more preferably between about 0.5 and about 1.5 GPa.

In some embodiments, the solidifying implant composition can be a solidifying polyurethane composition comprising an isocyanate, such as hydroxy-methylenediisocyanate (HMDI) and an alcohol, such as polycaprolactonediol (PCL diol). The compositions of the present invention are useful for treating patients by applying the solidifying implant composition to bone, reinforcing the bone structure, improving load bearing capacity and/or aiding healing of microfractures.

In some embodiments, where the solidifying implant composition is a solidifying polyurethane composition, the is ocyanate comprises a polyisocyanate. In some embodiments, the isocyanate comprises a diisocyanate. In some embodiments, the isocyanate comprises a hydroxymethylenediisocyanate (HMDI). In some embodiments where the solidifying implant composition is a solidifying polyurethane composition, the alcohol comprises a diol. In some embodiments, the alcohol comprises a polycaprolactone (PCL) diol. In some embodiments, the alcohol comprises a triol. In some embodiments, the alcohol comprises a polycaprolactone (PCL) triol.

One embodiment of the present invention comprises an injectable material comprised of a biocompatible, biodegradable polymers, optionally cross linked, optionally containing a filler material, optionally containing an amount of non-biodegradable polymeric material with properties of the final material being dependent on the relative amounts of the various components and their method of preparation. A table of the properties for the material is shown in Table 1.

In some embodiments, the polymers are prepared in situ after injection. In some embodiments, the polymer is prepared prior to injection.

The polymer may be prepared by radical polymerization, addition polymerization, the use of enzymes, or a combination thereof. The polymer may also be crosslinked. Crosslinking may be by radical reagents, by reactive functional groups, by two or by more different reactive functional groups. The polymer may be prepared by both polymerization and crosslinking.

In some embodiments, the material is prepared from prepolymers having multifunctional monomeric units. Alternatively or in addition, the polymers may have multifunctionality after preparation. In some embodiments, a solid filler material is injected with the monomer units of the prepolymer so that it is thoroughly mixed and forms a network with appropriate properties.

The present invention also provides for a method of treating a patient by implanting a polymeric implant composition and then solidifying the implant composition.

The present invention provides for a method of treating bone structures such as a fracture or other bone defect site in a patient by injecting the prepolymeric implant composition to bone (optionally mixed together with a filler, crosslinking agent or a biocompatible solvent). This reinforces the bone structure, improving load bearing capacity and aiding healing of microfractures.

The present invention provides for a method of fixing an implant, by applying a polymeric composition to reinforce the implant the implant.

The present invention provides for a method of devascularizing a tumor or vascular lesion by applying a polymeric implant composition to a tumor or vascular lesion.

The present invention also provides for a method of treating a vascular disease by applying polymeric implant composition to vascular site in need of treatment.

The present invention also provides for a method for creating stasis by applying polymeric implant composition to vascular site.

The present invention also provides for a method of treating aneurysms/pseudoaneurysms by applying a polymeric implant composition to an aneurysm/pseudoaneurysm.

DETAILED DESCRIPTION OF THE INVENTION

The present invention provides a solidifying implant composition for treating fractures, other bone conditions, and vascular diseases, generally including polymeric material, optionally mixed with fillers, therapeutic agents with or without a solvent carrier. In one preferred embodiment, the polymeric composition is mixed with a polar biocompatible solvent.

Before insertion into the body, the composition is in the form of an injectable fluid, paste, or a malleable putty. The composition solidifies when placed in contact with living tissue or liquid by absorption and diffusion of the solvent into the surrounding tissue or liquid, such that solidification is preferably temperature independent. However, solidification can also be temperature dependent.

The polymeric material (polymers and copolymers) used in the composition can include, but is not limited to, acrylics including polymethylmethacrylate (PMMA), polyethylene, polypropylene, polyesters, polybutyleneterephtalate (PBT), polystyrene mono- and copolymer, polybutadiene mono- and copolymer, polyvinyl alcohol mono- and copolymer, polyamides (nylon), polyglycolic acid (PGA), polylactic acid (PLA), polyglycolic-lactic acid (PGLA), polyurethanes, diacetonylacrylamide, polylactides, polydioxannones, polycarbonates, polyalkeneoxylates, polyanhydrides, polyamides, polyesteramides, polyurethanes, polyacetals, polyketals, polyorthocarbonates, polyphosphazenes, polyhydroxyvalerates, polyalkylene succinates, poly(malic acid), poly(amino acids), Chitin, Chitosan, polyorthoesters, polyhydroxybutyrates, polyethylene glycol, porous silicon, collagen, hyaluronic acid, and copolymers, terpolymers, and combinations of the above polymers. Multiple polymeric materials can be used in the composition, with or without solvents—or in combination with a single solvent or multiple solvents, as further described in the Examples below.

When a solvent used in the composition, the solvent can be any solvent that can dissolve the polymeric material, including water itself, and that is biocompatible and preferably bioabsorbable (i.e. able to be absorbed by the body), and can include, but is not limited to, dimethyl sulfoxide (DMSO), acetone, 2-butanol, ethanol, ethyl acetate, methyl acetate, dimethylformamide, caprolactam, oleic acid, 1 propanol, 2-propanol, propyl acetate, propylene glycol, glycerol, or any solvent analogous/homologous to dimethyl sulfoxide, and combinations thereof. The solvent can be in excess to dissolve polymers and other materials and yield variable viscosities that enhance ability to sculpt product to unique clinical situations that are present in each individual patient. When mixed, the solvent and polymer can form a hydrogel, aerosol gel, or other gel. The solvent can also optionally additionally include other solvents that are not bioabsorhable.

The composition can further include fillers or porogens, such as calcium phosphates (e.g., calcium phosphate particles, α-tricalcium phosphate, octacalcium phosphate), calcium sulphates, hydroxyapatite, silicates, or bioactive glasses. Additional examples of fillers include compounds providing calcium such as Ca(OH)$_2$, or CaCO$_3$, demineralized bone powder or particles, and coral powder.

The composition can further include polymeric, ceramic or metal fibers, filaments, coils, or particles, or combinations thereof as a filler, such as microparticles or nanofibers, which can increase structural and mechanical integrity, flexibility, durability, and cohesiveness of the resulting implant. Examples of ceramics are hydroxyapatite, calcium silicate, tri-calcium phosphate, biphasic calcium phosphate, or kaolin providing scaffolding for cellular in-growth and enhancing osseointegration.

Alternatively, or in addition, the compositions can further include radiopaque or radioactive isotope materials and particles such as, but not limited to, Tantalum, Platinum, Barium, Titanium, Silver, Gold, Palladium, Iridium, Osmium, Copper, Niobium, Molybdenum, Strontium and Gallium and/or alloys such as Nickel-Titanium, Nickel-Manganese-Gallium, Platinum-Iridium and Platinum-Osmium, and combinations thereof to enhance visualization of the injected material (act as contrast agents) and improve the structural integrity and performance of the implant. Visibility of these materials can degrade over time.

The composition can also further include a catalyst such as Stannous Octoate, Platinum, Palladium, peroxide, metal salts, Zinc, enzymes, redox couples, or combinations thereof to increase the speed of polymerization.

The composition can further include an initiator or initiator system. The initiator(s) may provide light curing, chemical curing, or a combination thereof. Non-limiting examples of photoinitiators include biocompatible photoinitiators such as beta carotene, riboflavin, Irgacure 651® (2,2-dimethoxy-2-phenylacetophenone), phenylglycine, dyes such as erythrosin, phloxime, rose bengal, thonine, camphorquinone, ethyl eosin, eosin, methylene blue, riboflavin, 2,2-dimethyl-2-phenylacetophenone, 2-methoxy-2-phenylacetophenone, 2,2-dimethoxy-2-phenyl acetophenone, and other acetophenone derivatives, and camphorquinone.

Non-limiting examples of chemical curing agents, e.g., free radical generators or oxidizing agents include peroxide compounds (i.e., peroxy compounds), including hydrogen peroxide as well as inorganic and organic peroxide compounds (e.g., "per" compounds or salts with peroxoanions such as benzoyl peroxide, phthaloyl peroxide, substituted benzoyl peroxides, acetyl peroxide, caproyl peroxide, lauroyl peroxide, cinnamoyl peroxide, acetyl benzoyl peroxide, methyl ethyl ketone peroxide, sodium peroxide, hydrogen peroxide, di-tea butyl peroxide, tetraline peroxide, urea peroxide, and cumene peroxide); hydroperoxides such as p-methane hydroperoxide, di-isopropyl-benzene hydroperoxide, tert-butyl hydroperoxide, methyl ethyl ketone hydroperoxide, and 1-hydroxy cyclohexyl hydroperoxide-1, ammonium persulfate, sodium perborate, sodium perchlorate, potassium persulfate, ozone, ozonides, 2-hydroxy-4-methoxy-benzophenone, 2 (2-hydroxy-5-methylphenyl) benzotriazol etc. Benzoyl peroxide is the preferred oxidizing agent. Other oxidizing agents include azo initiators, such as azoisobutyronitrile (AIBN) or 2,2-azobis(2-amidopropane) dihydrochloride. A reducing agent, or chemical accelerator may also be used. A desirable reducing agent is one that is sufficiently reducing in nature to readily react with the preferred oxidizing agent. A reducing agent has one or more functional groups for activation of the oxidizing agent. Preferably, such functional group(s) is selected from amines, mercaptans, or mixtures thereof. If more than one functional group is present, they may be part of the same compound or provided by different compounds. Non-limiting examples of reducing agents include tertiary aromatic amine (e.g., N,N-dimethyl-p-toluidine (DMPT) or N,N-bis(2-hydroxyethyl)-p-toluidine (DHEPT)), a mercaptan, which can include aromatic and/or aliphatic groups, and optionally polymerizable groups, sulfinic acids, formic acid, ascorbic acid, hydrazines, some alcohols, and salts thereof, can also be used herein to initiate free radical polymerization.

The composition can further include suspended particles of micro- or nano-scale biologically active material for localized targeted or non-targeted delivery. The biologically active material can be therapeutic agents or combinations of therapeutic agents such as proteins, drugs, or other agents. For example, antibiotics such as Vancomycin, Amikacin or Tetracycline and/or metals such as Silver or Copper can be included to prevent infection at an area to which the composition is applied. The biologically active material can be released specifically at the site of implantation of the composition. Thus, the composition can be used for site-specific delivery of therapeutic agents to stimulate or aid in bone healing such as bisphosphonates and hydroxyapatite. Pain relief therapeutics can be included such as paracetamol (acetaminophen), non-steroidal anti-inflammatory drugs (NSAIDs), and COX-2 inhibitors. Cancer treatments can also be included such as chemotherapeutics agents such as Methotrexate and inhibitors of cancer growth such as Gallium. These biologically active materials can be delivered buffered within the implant solution or within micro- or nanoparticles suspended within the implant. In some embodiments, the addition of biologically active material can be accomplished using the polymer synthesis techniques as described in U.S. Pat. No. 6,521,736, herein incorporated by reference.

The composition can further include biodegradable polymers, such as polyglycolic acid (PGA), polylactic acid (PLA), polyglycolic-lactic acid (PGLA), polycaprolactone (PCL), ε-poly-L-lysine (EPA), glycosaminoglycans (GAGS), polyalcohols, heparinoids, and combinations thereof that can initially prevent blood from clotting, provide cohesiveness and improve control during injection, create avenues for enhanced in-growth of supporting cells and improve healing by stimulating tissue ingrowth as they are degraded over time, and providing a mechanism for delivering targeted therapeutics via chemical attachment to side groups or encapsulation.

The composition can also further include a liquid contrast agent such as Ethiodol, and/or a powder such as Tantalum and/or Barium Sulfate, and/or an alloy such as Nickel-Titanium to enhance visualization of the material during implantation.

The hydrophobicity/hydrophilicity of the composition can be controlled. Preferably, the solidified composition is sufficiently hydrophilic that cells adhere well to the surface but sufficiently hydrophobic so as to "stick together" The hydrophobicity/hydrophilicity depends on a number of factors such as the hydrophobicity/hydrophilicity of the solidifiable prepolymer. The hydrophobicity of the prepolymer can be altered by adding or changing end groups on the compound.

The polymers' molecular structure can be systematically varied to produce a range of well-defined polymeric structures, for example, to result in a range of hydrophilic, hydrophobic, and complexing properties as described in U.S. Pat. No. 6,521,736, herein incorporated by reference in its entirety.

The viscosity of the composition depends on a number of factors such as the molecular weight of the ingredients in the prepolymer composition and the temperature. Typically, when the temperature is low, the curable admixture is more viscous; and, when the average molecular weight of the ingredients is high, it becomes more viscous. Different applications of the composition also require different viscosities. For example, to be injectable, the composition must be a free flowing liquid and, in other applications, it must be a moldable paste-like putty. The viscosity of the composition may be adjusted by formulating the prepolymer with a suitable amount of one or more biocompatible unsaturated functional monomers such as the ones described in U.S. Pat. Pub. 2003/114552 which are incorporated herein by reference.

The implant composition can be prepared by methods known in the art by mixing the polymeric material with the solvent and optionally any of the other compounds as described above. Many other materials can be added to provide the final composition with additional properties. Metals such as Tantalum and/or contrast agents such as Ethiodol can be added to the polymeric material and mixed immediately prior to injection, such as with Trufill n-Butyl Cyanoacrylate. Additionally, metals such as Tantalum can be added to the polymeric material during manufacture and agitated vigorously to suspend the metal immediately prior to injection. Additionally, various components such as polymeric material monomer, a contrast agent such as powdered Barium Sulfate, and antibiotics such as gentamicin can be added together and mixed injected. Furthermore, a first polymeric material (and optionally additional different polymeric material) can be mixed with a first solvent, and then a second, different polymeric material (and optionally additional different polymeric material) can be added with or without additional solvents as described in the Examples below.

In some embodiments, the polymer is prepared through enzymatic synthesis, such as described in U.S. Pat. No. 6,962,963 and in U.S. Patent Application Publication 2009/0099267, both of which are herein incorporated by reference.

In some embodiments, the polymer is prepared or cross-linked as described in U.S. Patent Application Publication 2011/013958, herein incorporated by reference.

In another embodiment, the composition can be a polyurethane composition. Generally speaking, polyurethanes are formed by reacting an isocyanate group, —N═C═O with a hydroxyl (alcohol) group, —OH. Polyurethanes are typically produced by the polyaddition reaction of a polyisocyanate with a polyalcohol (polyol) in the presence of a catalyst and other additives. In such cases, a polyisocyanate is a molecule with two or more isocyanate functional groups, R—(N═C═O)$_{n≥2}$ and a polyol is a molecule with two or more hydroxyl functional groups, R'—(OH)$_{n≥2}$. The reaction product is a polymer containing the urethane linkage, —RNHCOOR'—. Isocyanates will react with any molecule that contains an active hydrogen. In one preferred embodiment the isocyanate is hydroxymethylenediisocyanate (HMDI) and the hydroxy group is polycaprolactone (PCL) diol. Various additional reagents can be added, e.g., cross-linking agents, fillers, reaction accelerators or retardants.

The composition of the present device can be delivered in self-contained, single use, sterilized packaging that may need to be agitated to suspend metal contrast material prior to delivery.

The composition of the present invention can create an implant at provides support, stability, load bearing and fixation for fractures while at the same time dampening stress to prevent fracture of adjacent honey structures and allow controlled movement of the fractured bone that promotes faster and stronger healing of the fractured bone.

Once solidified, the composition acts as a scaffold for ingrowth and regeneration of bone tissue. The implant is capable of mimicking bone, vascular, and other tissue. The implant can be permanent, or can be biodegradable, or bioabsorbable. The composition of the present invention thus overcomes many of the drawbacks of compositions of the prior art.

The solidified composition possesses mechanical properties, which are improved upon the prior art for the applications of bone stabilization. The composition can have a structure such that is possesses compressive strength within the range of 10-500 MPa, it possesses elastic modulus between 0.1-100 GPa, and it possesses yield strength within 0.5-10 MPa. These properties improve strength, while dampening—but not entirely removing—stress to prevent weakening (stress shielding) and fracture of adjacent boney structures and allow controlled movement of the fractured bone that promotes faster and stronger healing of the fractured bone.

The consistency of the composition can be similar that of the natural tissue to absorb and decrease transfer of energy in order to promote normal function in the adjacent tissue. The consistency also allows surgical handling when the device is used as an adjunct to surgery.

The composition can have a structure that facilitates pore formation within and upon the surface of the implant within a range of 1-1000 µm (target mean pore size 50-150 µm) and <10 µm, respectively, in order to facilitate osteoblast ingrowth and protein absorption.

The solidified composition can possess degradation properties that facilitate the ingrowth of new tissue formation or release of therapeutics. These properties, such as the rate of degradation, can be controlled by material selection and pore sizes, connectivity, or volume to match degradation with bone growth or desired therapeutic release.

The composition is suitable for uses such as, but not limited to, vertebroplasty, kyphoplasty, void filling, bone stabilization, percutaneous injection, or stabilization of non resorbable and resorbable materials in contact with bone (fixation screws, gents, balloons, or implants) in mammals.

The composition of the present invention improves upon substances used in the prior art for other purposes for new applications discussed herein. A combination of a polymer and a solvent has been used in the past for other applications such as treating cerebrovascular diseases, specifically brain arteriovenous malformations and aneurysms, but the materials that are available are not cohesive and therefore are not effective for long-term treatment of fractures because they fall apart under stress. Hydroxyapatite has been used in similar applications, but lacks structural integrity to resist compression during load bearing. The composition of the present invention integrates the beneficial properties of disparate substances to provide a whole that is greater than the sum of the parts: each component supports the other components and yields a composite that combines the strength of each material while eliminating the inherent individual weaknesses. Thus, the composition of the present invention is a synergistic composition.

The composition of the present invention also provides the following additional advantages. The opacity of the material of the composition can diminish over time. When made to be radiopaque, the material can be delivered in particles, spheres, or liquids that degrade over time decreasing the radio density. The radiopaque material can be in suspension. This can include using nanoparticles to aid in the dissipation of the radiopaque material of a PEG or other polymeric material. The radiopaque material can lose its radiopacity over time. The composition of the present invention is a better liquid embolic than the prior art. Also, the combined benefits of using a solvent to deliver a polymeric material with a thermal responsive polymeric material or hydrogel decreases the volume or change the solvent needs, increases the control of the material and cohesiveness of the material, improving the effectiveness and safety of endovascular embolization.

The present invention provides for a method of treating patients, including all types of mammals, by implanting the composition of the polymeric material into bone, as described above, and solidifying the implant composition. The implantation or application of the composition can occur by methods that are routine in surgical procedures for orthopaedics, such as vertebroplasty or fixing fractures. In one preferred embodiment the composition is a polymeric material mixed with a bioabsorbable solvent. The composition can be administered in various ways, but preferably the implantation is performed by injecting the composition to the site of need. Hence, viscosity, absorption of solvent, etc. are critical parameters that can be adjusted depending on the use and environment. The composition can be premixed prior to injection, can be mixed in the injector device, can be mixed during injection, mixed in situ or a combination of these methods during the injection process. When mixed in situ, the composition and other components are caused to be mixed right at the site of application in the body. The composition can be injected with a needle with gauges including, but not limited to, down to a 22 gauge. For example, the composition can be injected with a needle gauge down to 14 gauge, down to 16 gauge, down to 20 gauge, or down to 22 gauge.

In the solidifying step, as described above, the implant composition can be solidified upon contact with surrounding tissue or liquid by absorbing and diffusing the solvent into the surrounding tissue or liquid. After the solvent has absorbed and diffused away, pores are formed in its place within and on the surface of the implant composition. Additionally the composition can be solidified using a cross linker, curing agent, enzyme, a thermosensitive polymer, or combination of the above or similar curing methods. The implant can remain in the body permanently, or it can be biodegradable or bioabsorbable.

This method can be used to treat a variety of medical conditions in procedures, such as, but not limited to, vertebroplasty, kyphoplasty, void filling, bone stabilization, or stabilization of nonresorbable materials in contact with bone (fixation screws or implants) in mammals.

Currently, there is no available product or method that addresses all types of bone fractures. This method can be used to treat bone fractures that can include, but are not limited to, bone fractures, osteoporotic bone fractures, compression fractures, stress fractures, pathological fractures, non-union fractures, complex fractures, displaced fractures, and poor-healing fractures.

The composition can also further absorb and distribute stress to prevent fatigue and fracture of adjacent bone. These characteristics improve durability of the implant composition.

The composition can also be used in a method of improving bone structure in patients, by applying the composition to bone, reinforcing bone structure and improving load bearing capacity and aiding healing of microfractures. The composition can also be temporarily stabilized after the bone structure has been reinforced. By this temporary stabilization, subsequent procedures can be made less difficult. The composition can be applied either by injecting the composition into or coating the composition on the bone or an implant. Preferably, this method is used to treat patients that are suffering from severe osteoporosis, metastases, or other bone lesions at risk of catastrophic failure. The solidified composition can remain in the body permanently, or it can be biodegradable or bioabsorbable.

The composition can further be used in a method of fixing an implant, by applying the composition to an implant, and reinforcing the implant. This method can be useful for stabilizing implants in the body. The solidified composition can remain in the body permanently, or it can be biodegradable or bioabsorbable.

The composition of the present invention can further be used in a method of devascularizing a tumor or vascular lesion, by applying the composition including a polymeric material to a tumor or vascular lesion. The tumor or vascular lesion can also further be treated with additional therapeutics, such as, but not limited to, chemotherapy, radiotherapy, or other cancer therapeutics.

The composition can further be used in vascular applications. The composition can also be used to address vascular diseases that currently have no effective or inadequate endovascular treatment options or improve upon existing endovascular treatment options. The composition can be applied to any area of a vascular site in need of treatment. This use can be applicable to endoleaks that occur following endovascular repair of aortic aneurysms, aneurysms, spinal and body arteriovenous malformations and fistulae, cerebral and spinal dural arteriovenous fistulae, traumatic vessel injury (traumatic vascular lesion), venous varices, visceral and/or viscerocutaneous fistulae and vascular tumors and improve treatment of cerebral arteriovenous malformations.

More specifically, the composition can be delivered into the space that is filled by blood or other body fluids and track along those avenues to find and fill the in-flow and out-flow of endoleak sacs, arteriovenous malformations and fistulae and varices at various sites in the body including the brain and spinal cord and their lining tissues, other organs and muscles, and viscera, or abnormal connections between viscera and skin.

Therefore, the composition of the present invention can also be used in a method of treating aneurysinsipseudoaneurysms by applying the composition including a polymeric material to an aneurysm/pseudoaneurysm.

There are several advantages to using the composition of the present invention in vascular applications. The composition can provide less invasive treatment of these very difficult lesions. The composition can also allow more precise control, improved visibility, time dependent radiopacity, and more efficacious treatment of these lesions.

In the method of the present invention, the compound of the present invention can be administered in various ways. Preferably, the composition is injected to the site of need. Hence, viscosity, absorption of solvent, etc. are critical parameters that can be adjusted depending on the use and environment. In vascular applications, the composition can also be delivered endovascularly to occlude arteries, veins, intervening vascular spaces, and abnormal connections or disruptions of blood vessels or viscera, or tumors of the body, spine or brain and surrounding structures.

Preferred polymers include polymers formulated with the following monomers either individually or in combination: lactic acid, glycolic acid, trimethylene carbonate, caprolactone, ethylene glycol, propylene glycol, hydroxybutyrate, propylene fumarate. Reactive materials can be produced from these polymers by fabricating them with reactive end groups such as isocyanates. Other reactive systems such as polypropylene fumarate or acrylate chemistry may be used to produce a two-part system that can be mixed immediately prior to injecting into the patient.

Fillers can be added for multiple purposes. A calcium phosphate additive will mimic bone and will impart osteo-conductivity on the material. The use of a resorbable material will aid bone ingrowth. Preferred materials are β tricalcium phosphate, α tricalcium phosphate, calcium carbonate, calcium sulfate or bioactive glasses. Basic materials such as calcium carbonate may have additional benefit in acting as a buffer against the acidic breakdown products of the polymer component. Fillers may also act to increase the stiffness of the material. Fillers may also be added to impart opacity to x-rays and other radiation, but this is not preferred in resorbable formulations. In these the calcium salt will impart a degree of x-ray opacity. This can be augmented by use of a transient material such as Iopamidol or Omnipaque which will provide xray opacity at the time of injection but which will subsequently diffuse out into the patient.

The table describes certain performance parameters that can be preferred in certain embodiments and/or applications.

Example 1

This invention is defined by its ability to control several important functional parameters of an injectable scaffold. This invention primarily features a polymer or co-polymer mix of biodegradable polymers, a crosslinking agent and, optionally, a solvent, e.g., a water miscible solvent. In this example, a PLA-PGA co-polymer with a triol cross-linker, such as glycerol, in a DMSO solvent was used. This combination is henceforth known as the "mix." The nature of the delivery of this scaffold is unique in that: the mix will retain its viscous liquid form prior to injection; upon injection and contact with bodily tissues and fluids the solvent will diffuse from the mix; and, as the solvent diffuses the cross-linked, cohesive co-polymer will be left behind.

Alone and uncontrolled, this co-polymer scaffold is mechanically limited. Controlling the ratio of PLA-PGA in this mix is essential in controlling not only the mechanical integrity, but also the degradation rate and porosity of the resulting scaffold.

TABLE 1

| Final Properties: | Preferred | More Preferred | Most Preferred | Comments |
|---|---|---|---|---|
| Compressive yield stress | | | | 100 MPa (cortical bone) |
| Compressive strength | Not critical as long as the material has a strain to yield greater than bone - the bone will protect the implant. | | | 5-60 MPa (cancellous) 140-200 MPa (cortical) |
| Compressive stiffness | .25-20 GPa | .3-2 GPa | .5-1.5 GPa | 0.7-1.5 GPa (cancellous) 14-20 GPa (cortical) |
| Strain to yield | >2.5% | >10% | >20% | 2.5% (cancellous) 1.5% (cortical) |
| Tensile strength | | | | 40-100 MPa (cortical) |
| Strength retention time | 6-26 weeks | 8-20 weeks | 10-14 weeks | |
| Degradation/ Resorption time | <60 months | 12-52 wks | 12-26 weeks | |
| Pore Size Porosity (%) | 10-500 μm | 20-300 μm | 50-150 μm | Porosity may not be immediately present, but may develop with time |
| Working time | 3 mins-5 hrs | 3-20 mins | 5-10 minutes | |
| Set time (75% of final stiffness) | 0.25-24 hrs | 1-5 hours | 0.25-2 hours | |
| Viscosity during injection | 0-7 × 10⁶ cP | | 100-500 cP | |

The invention is further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

PLA is comprised of polymeric chains of:

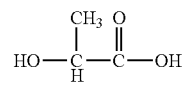

PGA is comprised of polymeric chains of:

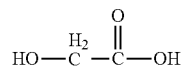

The ratio of these two polymers together in a ring opening or condensation reaction, in conjunction with controlling the stereochemistry of each individual polymer will play an important role primarily in controlling degradation rate. The COO ester groups on these polymers are essentially cleaved by esterases and water over time within the body, resulting in lactic acid and glycolic acid (which are naturally occurring materials). The CH3 group on PLA makes it slower to degrade than PGA. Therefore, increasing the ratio of PLA over PGA in a co-polymer results in a material that lasts longer in the body.

The glycerol cross-linker acts to crosslink the PLA-PGA co-polymer chains giving the scaffold structural integrity and cohesiveness. Drawn fibers of PLA or PLA can be used to increase the structural integrity. Because these chains are cross-linked, when the DMSO solvent diffuses from the injection, pores are created in place of the solvent.

Furthermore, the percentage of DMSO solvent used in the mix can control the viscosity of the injection prior to solidification. A decrease in solvent percentage results in a more viscous and more controlled, cohesive injection.

Based on the chemistry of these two polymers the mechanical integrity can be controlled minimally. Larger side groups (CH3 in PLA) result in increased mechanical integrity.

However, these polymers alone will not be mechanically strong (compressive strength) enough for application as a bone cement. To improve the mechanical strength and integrity of this mix, the use of additional materials and the bonds between these materials plays a primary role.

In this example, a polyHEMA (hydroxyethylmethacrylate) hydrogel, which has OH groups interacting with water, can be used in conjunction with the previously described mix. PolyHEMA is described chemically below:

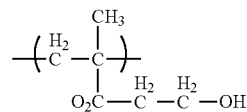

This hydrogel can be embedded with silicate or calcium phosphate salts/fibers/filaments/coils that significantly increase the mechanical strength of the material, based on the length of these fibers and the concentration of these fibers within the hydrogel. In conjunction with polyHEMA, a material like a silicate or hydroxyapatite can improve compressive strength due to the alignment of the molecular structure of the silicate itself. The nature of the polyHEMA can also act to retain these materials within the scaffold.

The hydrogel can either be cured as a hydrogel prior to injection and delivered into the body with the mix, or HEMA monomer can be added to the mix and injected. As the HEMA+mix+a redox partner and peroxide are injected and mixed together, the peroxide and a redox partner such as an enzyme, and HEMA undergoes a polymerization reaction resulting in a cured, cohesive polyHEMA structure embedded with the PLA-PGA co-polymer blend with little heat released.

Furthermore, additional materials, such as the aforementioned fibers, therapeutics encapsulated in nanoparticles or PEG, therapeutics alone, or radiopaque metal salts can be embedded in the mix or pre-cured hydrogel prior to injection. As the DMSO solvent is diffused from the scaffold or the polyHEMA chains are cured, these additional materials are captured within the scaffold. This provides a controlled release of targeted or non-targeted therapeutics (by degradation of polymer, release from nanoparticles, or diffusion from hydrogel), radiopaque visibility for ease of non-invasive injection, and increased mechanical properties due to fiber alignment.

Example 2

The material includes a polymeric composition in a biocompatible solvent. Such a polymeric composition can contain two biodegradable polymers combined as a copolymer, which are both soluble in the solvent. This can also contain a second composition including a monomer, which can be polymerized into a gel by a catalyst agent or a redox couple, which is mixed with the first composition. Additional insoluble particles can be added in the solvent solution or the gel for mechanical support of the resulting material.

Specifically, a first composition of PLA-co-PGA in a solvent, such as DMSO, can be combined with a second composition of a HEMA monomer. When these are combined, a catalyst, such as an enzyme or a redox couple ammonium persulphate (in composition 1) and ethylenediaminetetracetic acid (in composition 2), polymerize the HEMA into a gel. Insoluble particles, such as hydroxyapatite could then be mixed into the material either in the solvent or in the gel.

Example 3

The material includes a polymeric composition in a biocompatible solvent. Such a polymeric composition can contain two biodegradable polymers, which are both soluble in the solvent. This can also contain a second composition comprising a monomer, which can be polymerized by a catalyst agent or a redox couple, which is mixed with the first composition. Additional insoluble particles can be added in the solvent solution or the gel for mechanical support of the resulting material.

Specifically, a composition of PLA and PCL in a solvent, such as DMSO, can be combined with a second composition of an AA (acrylic acid) monomer. When these are combined, a catalyst, such as an enzyme or a redox couple—ammonium persulphate (in composition 1) and ethylenediaminetetracetic acid (in composition 2), polymerize the AA. Insoluble particles, such as hydroxyapatite can then be mixed into the material either in the solvent or in the gel.

Example 4

The material includes a polymeric composition in a biocompatible solvent. Such a polymeric composition can contain two biodegradable polymers, which are both soluble in the solvent. This can also contain a second composition of monomers, which can be polymerized into a gel by a catalyst agent or a redox couple, which is mixed with the first composition. Additional insoluble particles can be added in the solvent solution or the gel for mechanical support of the resulting material.

Specifically, a composition of PLA and PCL in a solvent, such as DMSO, can be combined with a second composition comprising a HEMA and AA monomers. When these are combined, a catalyst, such as an enzyme or a redox couple—ammonium persulphate (in composition 1) and ethylenediaminetetracetic acid (in composition 2), can polymerize the HEMA and AA into a gel. Insoluble particles, such as hydroxyapatite can then be mixed into the material either in the solvent or in the gel.

Example 5

The material includes a polymeric composition in a biocompatible solvent. Such a polymeric composition can contain two biodegradable polymers combined as a copolymer, which are both soluble in the solvent. This can also contain a second composition of a monomer, which can be polymerized into a gel by a catalyst agent or a redox couple, which is mixed with the first composition. Additional insoluble particles can be added in the solvent solution or the gel for mechanical support of the resulting material.

Specifically, a composition of PLA-co-PGA in a solvent, such as DMSO, can be combined with a second composition comprising an AA monomer. When these are combined, a catalyst, such as an enzyme or a redox couple—ammonium persulphate (in composition 1) and ethylenediaminetetracetic acid (in composition 2), polymerize the AA into a gel. Insoluble particles, such as hydroxyapatite could then be mixed into the material either in the solvent or in the gel.

Example 6

The material includes a polymeric composition in a biocompatible solvent. Such a polymeric composition can contain two biodegradable polymers, which are both soluble in the solvent. This can also contain a second composition of an already polymerized hydrogel material, which is mixed with the first composition. Additional insoluble particles can be added in the solvent solution or the gel for mechanical support of the resulting material.

Specifically, a composition of PLA and PCL in a solvent, such as DMSO, can be combined with a second composition comprising a polyHEMA hydrogel and PEG. Insoluble particles, such as hydroxyapatite can then be mixed into the material either in the solvent or in the gel.

Example 7

The material includes a polymeric composition in a biocompatible solvent. Such a polymeric composition can contain two biodegradable polymers, which are both soluble in the solvent. This can also contain a second composition of an already polymerized hydrogel material, which is mixed with the first composition. Additional insoluble particles can be added in the solvent solution or the gel for mechanical support of the resulting material.

Specifically, a composition of PLA and PCL in a solvent, such as DMSO, can be combined with a second composition of a polyAA hydrogel and PEG. Insoluble particles, such as hydroxyapatite can then be mixed into the material either in the solvent or in the gel.

Example 8

This example illustrates the preparation of a bone augmentation or vascular embolization injectable composition (A1). Poly(ethylene-co-vinyl alcohol) (EVOH) was ground to <2 mm diameter particles and dried under vacuum. 240 mg EVOH was solubilized in 2 grams of dimethyl sulfoxide (DMSO). At 37 degrees C., 880 mg hydroxymethyleriediisocyanate (HMDI) was mixed with the EVOH-DMSO solution. It had a working time of 2 hours. Samples were held in saline at 37 degrees C. to mimic the body and allow solvent exchange. Samples were tested after 12 hours. The resulting material was a soft, cohesive gel.

Example 9

This example illustrates the preparation of another bone augmentation injectable composition (A2). EVOH was ground to <2 mm diameter particles. Calcium carbonate and EVOH were dried under vacuum. 240 mg EVOH was solubilized in 2 g DMSO. 1 gram of calcium carbonate was mixed into to the EVOH-DMSO solution. At 37 degrees C., 880 mg HMDI was mixed with the solution. Within 2 hours, a soft, cohesive gel formed. Injection into water rapidly increased hardness. It had a working time of 3 hours and increased hardened within 4 hours. Samples were held in saline at 37 degrees C. to mimic the body and allow solvent exchange. Samples were tested after 12 hours. The final material had hardness up to 50 Shore D.

Example 10

This example illustrates the preparation of another bone augmentation or vascular embolization injectable composition (B1). EVOH was ground to <2 mm diameter particles and dried under vacuum. 440 mg EVOH was solubilized in 2 g DMSO. 90 mg ammonium persulfate (APS) was solubilized in 1 g DMSO separately. 230 mg methylene bisacrylamide (MBA) was solubilized in 1 g DMSO separately. At 37 degrees C., the three solutions were mixed. The mixture had a working time of 4 hours. Samples were held in saline at 37 degrees C. to mimic the body and allow solvent exchange. The resulting material was a resilient gel with a hardness of 10 Shore D.

Example 11

This example illustrates another preparation of a bone augmentation injectable composition (B2). EVOH was ground to <2 mm diameter particles. Hydroxyapatite and EVOH were dried under vacuum. 440 mg EVOH was solubilized in 2 g DMSO. 1 gram of hydroxyapatite was mixed with the EVOH-DMSO solution. 90 mg APS was solubilized in 1 g DMSO separately. 230 mg MBA was solubilized in 1 g DMSO separately. At 37 degrees C., three solutions were mixed. The mixture had a working time of 4 hours. Samples were held in saline at 37 degrees C. to mimic the body and allow solvent exchange. Samples were tested after 12 hours. The resulting material was a resilient gel.

Example 12

Preparation of Bone Augmentation Injectable (B3). EVOH was ground to <2 mm diameter particles. Calcium carbonate and EVOH were dried under vacuum. 440 mg EVOH was solubilized in 2 g DMSO. 1 g calcium carbonate was mixed with the EVOH-DMSO solution. 90 mg APS was solubilized in 1 g DMSO separately. 230 mg MBA was solubilized in 1 g DMSO separately. At 37 degrees C., three solutions were mixed. The mixture had a working time of 4 hours. Samples were held in saline at 37 degrees C. to mimic the body and allow solvent exchange. Samples were tested after 12 hours. The resulting material was a resilient gel with hardness of 45 Shore D.

Example 13

Preparation of Bone Augmentation. Prepolymer. Polycaprolactone (PCL) diol was dried under vacuum. 1.76 g PCL dial was mixed with 1 g DMSO and then with 1.68 g hydroxymethyldiisocyanate (HMDI) and 10 mg Sn ethylhexarioate (SnOct) at 70 degrees C. After 20 minutes the solution was removed from heat and stored at room temperature.

Example 14

This example illustrates the preparation of another bone augmentation injectable composition (C1). Calcium carbonate was dried under vacuum. The prepolymer from Example 13 was mixed with 1 g PCL triol at 37 degrees C. The mixture was injected into a mold at 37 C. It had a working time of 60 minutes and hardened within 2 hours. Samples were held in saline at 37 degrees C. to mimic the body and allow solvent exchange. Samples were tested after 12 hours. The resulting material was clear and resilient and had hardness of 10 Shore D.

Example 15

Preparation of Bone Augmentation Injectable C2: Calcium carbonate was dried under vacuum. The prepolymer from Example 13 was reheated to 37 degrees C. 1 g calcium carbonate and 1 g PCLtriol were added to the prepolymer. It had a working time of 60 minutes and hardened within 2 hours. Samples were held in saline at 37 degrees C. to mimic the body and allow solvent exchange. Samples were held in saline at 37 degrees C. to mimic the body and allow solvent exchange. Samples were tested after 12 hours. The resulting material was white and resilient and had hardness of 17 Shore D.

Example 16

Preparation of Bone Augmentation Injectable C3: Calcium carbonate was dried under vacuum. The prepolymer from Example 13 was reheated to 37 degrees C. 3 g calcium carbonate and 1 g PCLtriol were added to the prepolymer. It had a working time of 60 minutes and hardened within 2 hours. Samples were held in saline at 37 degrees C. to mimic the body and allow solvent exchange. Samples were held in saline at 37 degrees C. to mimic the body and allow solvent exchange. Samples were tested after 12 hours. The resulting material was white and resilient and had hardness of 30 Shore D.

Example 17

Preparation of Bone Augmentation Injectable D1:
Beta-tricalcium phosphate (β-TCP) was dried under vacuum. The prepolymer from Example 13 was reheated to 37 degrees C. 2 g β-TCP and 1 g PCLtriol were added to the prepolymer, and then transferred to a mold. It had a short working time and hardened within hours. Samples were held in saline at 37 degrees C. to mimic the body and allow solvent exchange. Samples were held in saline at 37 degrees C. to mimic the body and allow solvent exchange. Samples were tested after 12 hours. The resulting material was white and resilient.

Example 18

Preparation of Bone Augmentation Injectable D2: Beta-tricalcium phosphate (β-TCP) was dried under vacuum. The prepolymer from Example 13 was reheated to 37 degrees C. 6 g (β-TCP was added to the prepolymer, then it was transferred to a mold. It had a short working time and hardened within hours. Samples were held in saline at 37 degrees C. to mimic the body and allow solvent exchange. Samples were held in saline at 37 degrees C. to mimic the body and allow solvent exchange. Samples were tested after 12 hours. The resulting material was white and resilient.

Example 19

Preparation of Bone Augmentation Injectable D3: Three g of the material was taken from Example 18 immediately after mixing. It was mixed with 1 g DMSO at 37 degrees C., then transferred to a mold. It had a short working time and hardened within hours. Samples were held in saline at 37 degrees C. to mimic the body and allow solvent exchange. Samples were tested after 12 hours. The resulting material was white and resilient.

Example 20

Preparation of Bone Augmentation Injectable D4: Beta-tricalcium phosphate (β-TCP) was dried under vacuum. The prepolymer from Example VI was reheated to 37 degrees C. 6 g β-TCP and 1 g PCLtriol were added to the prepolymer, and then transferred to a mold. It had a short working time and hardened within hours. Samples were held in saline at 37 degrees C. to mimic the body and allow solvent exchange. Samples were tested after 12 hours. The resulting material was white and resilient.

Example 21

Preparation of Bone Augmentation Injectable D5: Three grams of the material was taken from Example 20 immediately after mixing it was mixed with 1 g DMSO at 37 degrees C., and then transferred to a mold. It had a short working time and hardened within hours. Samples were held in saline at 37 degrees C. to mimic the body and allow solvent exchange. Samples were tested after 12 hours. The resulting material was white and resilient.

Example 22

Preparation of Bone Augmentation Prepolymer without Solvent: PCLdiol was dried under vacuum. 1.76 g PCLdiol was mixed with 1.68 g HMDI at 70 degrees C. After 20 minutes the solution was removed from heat and stored at room temperature.

Example 23

Preparation of Bone Augmentation Prepolymer without Solvent:
PCL diol was dried under vacuum. 1.76 g PCL diol was mixed with 1.68 g HMDI and 1 mg SnOct at 70 degrees C. After 20 minutes the solution was removed from heat and stored at room temperature.

With the above examples, in addition other combinations of the same materials can be utilized to improve the properties of the bone cement. Other biodegradable and non-degradable polymer combinations can also be utilized.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A bone implant for bone augmentation or treatment of a bone fracture or lesion comprising:
    i) a biocompatible, biodegradable polymer;
    ii) a porogen including fibers;
    wherein the bone implant has a surface having pores of <10 μm for facilitating osteoblast ingrowth; and
    the bone implant has or develops a scaffold for ingrowth and regeneration of bone tissue.

2. The bone implant of claim 1, wherein the fibers include fibers that are aligned and is formed of a resorbable material.

3. The bone implant of claim 1, wherein the biocompatible and biodegradable polymer incudes a polyesters, a polyvinyl alcohol, a polyglycolic acid (PGA), a polylactic acid (PLA), a polyglycolic-lactic acid (PGLA), a polyhydroxyvalerates, a poly(amino acids), Chitin, Chitosan, polyhydroxybutyrates, polyethylene glycol, or a copolymer, a terpolymers, or any combinations of the above polymers.

4. The bone implant of claim 1, wherein the biocompatible and biodegradable polymer includes one or more monomers selected from the group consisting of lactic acid, glycolic acid, trimethylene carbonate, caprolactone, ethylene glycol, propylene glycol, hydroxybutyrate, and propylene fumarate.

5. The bone implant of claim 1, wherein degradation of the porogen forms an interconnective pore structure.

6. The bone implant of claim 5, wherein the bone implant develops pores having a size of 10 to 500 μm.

7. The bone implant of claim 1, wherein the bone implant comprises an additional porogen in the form of particles.

8. The bone implant of claim 1, wherein the bone implant provides support, stability load bearing and fixation for fractures while dampening stress to prevent fracture of adjacent boney structures and allow controlled movement of the fractured bone that promotes healing of the fractured bone.

9. The bone implant of claim 1, wherein the bone implant is characterized by a strain to yield of greater than 2.5%.

10. The bone implant of claim 9, wherein the bone implant is characterized by a compressive stiffness of 14-20 GPa.

11. The bone implant of claim 1, wherein the bone implant includes a biologically active material for localized delivery.

12. The bone implant of claim 11, wherein the biologically active material is a targeted therapeutic and the bone implant provides a controlled release of the targeted therapeutic.

13. The bone implant of claim 11, wherein the biologically active material includes a therapeutic agent.

14. The bone implant of claim 13, wherein the therapeutic agent incudes a chemotherapeutic agent.

15. The bone implant of claim 1, wherein the bone implant includes a hydrogel.

16. The bone implant of claim 1, wherein the biocompatible and biodegradable polymer is cross-linked.

17. The bone implant of claim 1, wherein
    the fibers include fibers that are aligned and is formed of a resorbable material;
    the biocompatible and biodegradable polymer includes one or more monomers selected from the group consisting of lactic acid, glycolic acid, trimethylene carbonate, caprolactone, ethylene glycol, propylene glycol, hydroxybutyrate, and propylene fumarate;
    a degradation of the porogen forms an interconnective pore structure including pores having a size of 10 to 500 μm;
    the bone implant is characterized by a strain to yield of greater than 2.5%; the bone implant is characterized by a compressive stiffness of 14-20 GPa.

18. The bone implant of claim 17, wherein the bone implant is characterized by a strain to yield of greater than 10%; the porogen includes a silicate or a phosphate.

19. A bone implant for bone augmentation or treatment of a bone fracture or a lesion comprising:
    i) a biocompatible, biodegradable polymer;
    ii) a porogen including particles;
    wherein the bone implant has a surface having pores of <10 μm for facilitating osteoblast ingrowth; and
    the bone implant has or develops a scaffold for ingrowth and regeneration of bone tissue.

20. A method for forming a bone implant comprising the steps of:
    i) applying a composition comprising a polymer, a porogen, and a solvent to a bone;
    ii) removing the solvent to form a porous surface characterized by a pore size of <10 μm; wherein
    the porogen includes aligned fibers;
    the bone implant degrades to form interconnected pores having a pore size of 10 to 500 μm; and
    the bone implant is characterized by a strain to yield of greater than 2.5% and a compressive stiffness of 14-20 GPa.

* * * * *